United States Patent [19]

Bonaldi et al.

[11] Patent Number: 5,650,522

[45] Date of Patent: Jul. 22, 1997

[54] PROCESS FOR THE PREPARATION OF α-METHYL-2-THIOPHENEACETIC ACID DERIVATIVES

[75] Inventors: Antonio Bonaldi, Chiuduno; Massimo Ferrari, Cenate Sotto; Egidio Molinari, Longone Al Segrino; Fabrizio Zinetti, Casazza, all of Italy

[73] Assignee: Erregierre S.P.A., Milan, Italy

[21] Appl. No.: 663,953

[22] Filed: Jun. 14, 1996

[30] Foreign Application Priority Data

Jun. 16, 1995 [IT] Italy .................. MI95A1297

[51] Int. Cl.⁶ .................................. C07D 333/22
[52] U.S. Cl. .................................. 549/72; 549/73
[58] Field of Search .......................... 549/72, 73

[56] References Cited

U.S. PATENT DOCUMENTS

| | | | |
|---|---|---|---|
| 4,159,986 | 7/1979 | Clémence et al. | 549/72 |
| 4,690,945 | 9/1987 | Arechaga et al. | 514/448 |
| 5,073,184 | 12/1991 | Anthony et al. | 549/73 |

FOREIGN PATENT DOCUMENTS

| | | |
|---|---|---|
| 1201442 | 12/1982 | Canada . |
| 0248107 | 12/1987 | European Pat. Off. . |
| 2398068 | 7/1978 | France . |
| 2 132 607 | 7/1984 | United Kingdom . |

OTHER PUBLICATIONS

European Journal of Medicinal Chemistrychimica Therapeutical. vol. 9, No. 4, 1974, Paris, France, pp. 390–396.

"Advanced Organic Chemistry; Reactions, Mechanisms, and Structure" Third Edition, 1985, John Wiley & Sons, Inc, New York. US.

Primary Examiner—José G. Dees
Assistant Examiner—Mary C. Cebulak
Attorney, Agent, or Firm—Lowe, Price, LeBlanc & Becker

[57] ABSTRACT

Process for the preparation of derivatives having general formula (I)

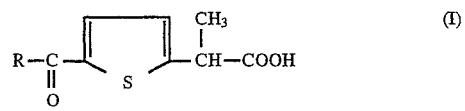

wherein the meaning of R will be defined in the text, characterized by the reaction between a compound having formula

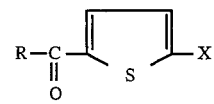

wherein X is an halogen, and an alkaline salt of a methyl dialkylmalonate.

6 Claims, No Drawings

PROCESS FOR THE PREPARATION OF α-METHYL-2-THIOPHENEACETIC ACID DERIVATIVES

PRIOR ART

Several processes for the preparation of the α-methyl-2-thiopheneacetic acid derivatives are known.

All the known processes use the α-methyl-2-thiopheneacetic acid as intermediate product (Bull. Soc. Chem. France 1961. p. 1820; French Patent Application N.2398068; Canadian Patent N.1201442).

The preparation of said intermediate shows several drawbacks being based on very laborious and low yield processes contemplating very expensive or very dangerous reactants such as sodium cyanide.

Moreover the final reaction with the α-methyl-2-thiopheneacetic acid to obtain the desired derivative is not selective and so a laborious final separation of the undesired by-product with lowering of the yield is required.

SUMMARY

Now a new process for the preparation of the α-methyl-2-thiopheneacetic acid derivatives has been found, allowing to overcome the drawbacks of the prior art.

Said derivatives have general formula (I)

$$R-\underset{\underset{O}{\|}}{C}-\underset{S}{\text{[thiophene]}}-\underset{\underset{CH_3}{|}}{CH}-COOH \quad (I)$$

wherein R is an alkyl group from C1 to C5 or an aryl group

[aryl group with RI and RII substituents]

wherein RI and RII are hydrogen or alkyl groups from C1 to C4 or halogens or nitro groups or alkyloxy groups as $CH_3O$, $CH_3$—$CH_2$—O.

The process for the preparation of the derivatives is realized by the following steps:

a) a compound having formula

[thiophene with X]

wherein X is an halogen, is reacted with a compound having formula $RCOCl$ or $(RCO)_2O$ in presence of a Lewis acid to obtain the compound (II)

$$R-\underset{\underset{O}{\|}}{C}-\underset{S}{\text{[thiophene]}}-X \quad (II)$$

b) the compound (II) is reacted with a compound having formula (III)

$$CH_3-C\underset{\diagdown COOR^{III}}{\overset{\diagup COOR^{III}}{\underset{M}{|}}} \quad (III)$$

wherein RIII is an alkyl group from C1 to C4 or an aryl group and M is an alkaline metal, to obtain the compound (IA)

$$R-\underset{\underset{O}{\|}}{C}-\underset{S}{\text{[thiophene]}}-\underset{\underset{COOR^{III}}{|}}{\overset{\overset{COOR^{III}}{|}}{C}}-CH_3 \quad (IA)$$

c) the compound (IA) is saponified with alkali and subsequently it is treated with a mineral acid obtaining the compound (I).

DETAILED DESCRIPTION OF THE INVENTION

The characteristics and the advantages of the process for the preparation of the α-methyl-2-thiopheneacetic derivatives according to the present invention will be better pointed out during the following detailed description.

Said derivatives have general Formula (I)

$$R-\underset{\underset{O}{\|}}{C}-\underset{S}{\text{[thiophene]}}-\underset{\underset{CH_3}{|}}{CH}-COOH \quad (I)$$

wherein R is an alkyl group from C1 to C5 or an aryl group

[aryl group with RI and RII substituents]

wherein RI and RII are hydrogen or alkyl groups from C1 to C4 or halogens or nitro groups or alkyloxy groups as $CH_3O$, $CH_3$—$CH_2$—O.

The process for the preparation of the derivatives (I) according to the present invention uses as starting compound

[thiophene with X]

wherein X is an halogen, preferably Br, which is a product easily available in the market.

Said starting product is reacted with a compound having formula $RCOCl$ or $(RCO)_2O$, wherein R has the above described meaning, in presence of a Lewis acid such as $AlCl_3$, $ZnCl_2$ and $BF_3$.

The compounds having formula (II)

$$R-\underset{\underset{O}{\|}}{C}-\underset{S}{\text{[thiophene]}}-X$$

wherein R and X have the above defined meaning are obtained from this reaction with a nearly quantitative yield.

The compounds having formula (II) are easily crystallizable solids and therefore they are easily isolable and purifiable.

Commonly used solvents such as the methylene chloride, the dichloro ethane, the carbon disulfide etc. are used for the reaction.

The reaction temperature is not critical and it may be in the range from 0° C. to the temperature of the used solvent.

Preferably the reaction temperature ranges from 30° C. to 50° C. For the preparation of the compound (I) an alkaline salt of a methyl dialkylmalonate (III) (preferably methyl diethylmalonate, easily available in the market) is reacted with the compound (II) according to the following scheme:

$$R-\overset{\|}{\underset{O}{C}}-\underset{II}{\boxed{\phantom{S}}_S}-X + M-\overset{COOR^{III}}{\underset{COOR^{III}}{\overset{|}{C}-CH_3}} \longrightarrow$$

$$R-\overset{\|}{\underset{O}{C}}-\underset{IA}{\boxed{\phantom{S}}_S}-\overset{COOR^{III}}{\underset{COOR^{III}}{\overset{|}{C}-CH_3}} + MX$$

wherein R and X have the above defined meaning, M is an alkaline metal selected from Na, K and Li and RIII is an alkyl group from C1 to C4 or an aryl group.

The reaction is carried out in an aprotic solvent selected from the group consisting of dimethylformamide, dimethylethyl acetamide, dimethyl sulfoxide, benzene, toluene, xylene, dioxane, dimethoxy ethane, diethylene glycol, dimethyl ether, triethylamine, tributylamine.

The reaction may be carried out indifferently either adding the alkaline salt of the methyl diethylmalonate (III) to the solution of the compound (II) or acting inversely that is adding the solution of the compound (II) to the methyl diethylmalonate alkaline salt.

The reaction temperature is not critical and it is acted preferably between 40° and 120° C.

Lower temperatures extend too much the reaction times.

The compound (IA) obtained from the described reaction is saponified by treatment with sodium hydroxide or potassium hydroxide in an aqueous solution.

At the end of the saponification the mixture is acidified with a mineral acid such as hydrochloric acid, sulfuric acid etc., obtaining the compound (I) which is isolated and purified according to the known techniques.

It must be noticed that during the saponification the decarboxylation with formation of the desired product according to the following scheme occurs too.

$$R-\overset{\|}{\underset{O}{C}}-\boxed{\phantom{S}}_S-\overset{COOR^{III}}{\underset{COOR^{III}}{\overset{|}{C}-CH_3}} - 2OH^- \cdots\cdots>$$

$$R-\overset{\|}{\underset{O}{C}}-\boxed{\phantom{S}}_S-\overset{COO^-}{\underset{COO^-}{\overset{|}{C}-CH_3}} +$$

$$2ROH \underset{+H_2O}{\cdots\cdots} R-\overset{\|}{\underset{O}{C}}-\boxed{\phantom{S}}_S-\overset{CH^3}{\underset{COO^-}{\overset{|}{CH}}} - HCO_3^-$$

The process according to the invention results much easier, less dangerous and cheaper than the known processes and moreover it leads to the formation of final products having higher purity which therefore do not need particular purifications to be used in the pharmaceutical field.

Said process is particularly useful for the preparation of the tiaprofenic acid (5-benzoyl-α-methyl-2-thiopheneacetic acid) which is a very important pharmaceutical compound having anti-inflammatory and analgesic activity.

The following experimental examples are reported for illustrative but not limitative aim of the present invention.

EXAMPLE 1

Preparation of the 5-benzoyl-α-methyl-2-thiopheneacetic acid.

3.420 kg of benzoyl chloride are slowly added to a suspension of 3.250 kg of aluminum trichloride in 12 kg of methylene chloride, between 10° and 20° C.

At the end the mixture is stirred for 10 minutes and then 3.600 kg of 2-bromothiophene are slowly added between 0° and 5° C.

The mixture is stirred for 1 hour at 15° C. and then it is poured into a mixture of ice, water and hydrogen chloride. The organic phase is separated and dry concentrated and the residual product is crystallized from sec-butanol and dried. 5.500 kg of 5-benzoyl-2-bromothiophene with m.p. 73°–75° C. and HPLC purity>99% are obtained. Yield equal to 92.7%.

260 of methyl diethylmalonate are slowly added, maintaining the temperature between 10° and 20° C., to a suspension of 54 g of sodium hydride at 60% in 600 g of dimethylformamide. At the end the mixture is stirred for 2 hours at 20° C. in order to complete the formation of the sodium methyl diethylmalonate.

A solution separately prepared dissolving 300 g of 5-benzoyl-2-bromothiophene in 600 ml of dimethylformamide is slowly added letting the temperature raise to 80° C. At the end the reaction mixture is maintained at this temperature for more than 2 hours.

The mixture is then cooled at 30° C. and 500 g of toluene and 1500 g of water are added.

The phases are separated, the aqueous one is removed and the organic one is washed with 500 ml of water and the aqueous phase is removed again.

The organic phase is dry concentrated and the residual oil is treated with 500 g of methanol.

The obtained solution is reflux warmed and 500 g of 30% sodium hydroxide are added for the saponification. When the addition is over the mixture is reflux maintained for 1 hour and then it is distilled in order to remove all the methanol.

800 g of water and 800 g of toluene are added and the mixture is acidified with sulfuric acid to pH 2–3.

The aqueous phase is removed and the organic one is washed with water and the aqueous phase is removed again. The organic phase is dry vacuum concentrated and the residue is treated with 1500 g of acetone.

50 g of isopropylamine are then added to the acetone solution. The salt of isopropylamine of 5-benzoyl-α-methyl-2-thiopheneacetic acid precipitates and is filtered at 0° C. and accurately washed with acetone.

The so obtained salt is dissolved in 1000 g of deionized water, the solution is treated with decolorizing carbon and then acidified with diluted phosphoric acid to pH 3.

The pure 5-benzoyl-α-methyl-2-thiopheneacetic acid precipitates and is filtered, accurately washed with water and dried to 50° C.

305 g of a white product having the following characteristics are obtained: titre 99.98%, HPLC purity 99.9%.

EXAMPLE 2

The Example 1 has been repeated with the difference that toluene has been used instead of the dimethyl-formamide for the reaction between the sodium methyl diethylmalonate and the 5-benzoyl-2-bromothiophene. A product having the same characteristics of the Example 1 has been obtained.

EXAMPLE 3

The Example 1 has been repeated with the difference that the reaction between the sodium methyl diethylmalonate and the 5-benzoyl-2-bromothiophene has been carried out adding the solution of the sodium methyl diethylmalonate to the solution of the 5-benzoyl-2-bromothiophene.

A product having the same characteristics of the Example 1 has been obtained with a slightly higher yield.

EXAMPLE 4

The example 1 has been repeated with the difference that the raw product has been purified by the following method.

After the saponification the product has been precipitated by treatment with a solution of sulfuric acid and then dissolved again with a solution of sodium carbonate.

The obtained solution has been extracted with toluene, treated with active carbon and finally treated with a solution of sulfuric acid. A product having good quality but not perfectly white has been obtained.

EXAMPLE 5

Preparation of the 5-acetyl-α-methyl-2-thiopheneacetic acid.

This preparation has been carried out according to the method described in the Example 1 using acetyl chloride instead of the benzoyl chloride, in an equivalent quantity.

The obtained product had a HPLC purity of the 99.9%.

We claim:

1. Process for the preparation of the α-methyl-2-thiopheneacetic acid derivatives having general formula (I)

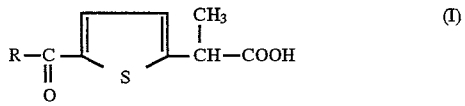

wherein R is an alkyl group from C1 to C5 or an aryl group

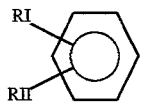

wherein RI and RII are hydrogen or alkyl groups from C1 to C4 or halogens or nitro groups, or methyloxy or ethyloxy groups, characterized by the following steps:

a) a compound having formula

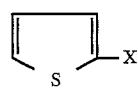

wherein X is an halogen, reacted with a compound having formula RCOCl or (RCO)$_2$O in presence of a Lewis acid to obtain the compound (II)

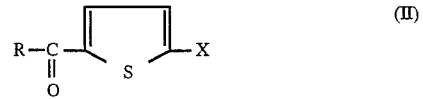

b) the compound (II) is reacted with a compound having formula (III)

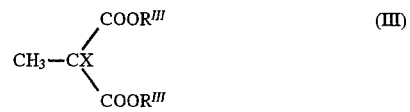

wherein RIII is an alkyl group from C1 to C4 or an aryl group and M is an alkaline metal, to obtain the compound (IA)

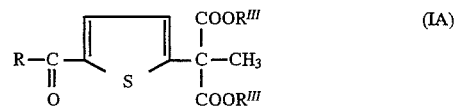

c) the compound (IA) is saponified with alkali and subsequently it is treated with a mineral acid obtaining the compound (I).

2. Process as claimed in claim 1, characterized in that said Lewis acid used in the step a) is selected from the group consisting of AlCl$_3$, ZnCl$_2$ and BF$_3$.

3. Process as claimed in claim 1, characterized in that the reaction of the step a) is carried out in a solvent selected from the group consisting of methylene chloride, dichloroethane and carbon disulfide.

4. Process as claimed in claim 1, characterized in that the reaction of the step a) is carried out at a temperature ranging from 30° to 50° C.

5. Process as claimed in claim 1, characterized in that the reaction of the step b) is carried out in a solvent selected from the group consisting of dimethylformamide, dimethylethyl acetamide, dimethyl sulfoxide, benzene, toluene, xylene, dioxane, dimethoxy ethane, diethylene glycol, dimethyl ether, triethylamine and tributylamine.

6. Process as claimed in claim 1, characterized in that the reaction of the step b) is carried out at a temperature ranging from 40° to 120° C.

* * * * *